United States Patent [19]

Shimizu et al.

[11] Patent Number: 5,591,334
[45] Date of Patent: Jan. 7, 1997

[54] APPARATUS FOR GENERATING NEGATIVE IONS

[75] Inventors: Shigeki Shimizu, Tokyo, Japan; Bang W. Lee, Seoul, Rep. of Korea

[73] Assignee: Geochto Ltd., Tokyo, Japan

[21] Appl. No.: 322,306

[22] Filed: Oct. 4, 1994

[30] Foreign Application Priority Data

Oct. 19, 1993 [JP] Japan ................................ 5-261396
Nov. 26, 1993 [JP] Japan ................................ 5-295812

[51] Int. Cl.$^6$ .............................. B01D 21/26; H05F 3/00
[52] U.S. Cl. ................ 210/243; 210/294; 210/512.1; 204/164; 204/194; 96/62; 96/64; 96/95; 96/97
[58] Field of Search .................................. 96/62, 64, 95, 96/97; 204/164, 194; 210/294, 512.1, 243

[56] References Cited

U.S. PATENT DOCUMENTS

| 4,236,900 | 12/1989 | Fitch et al. ................................ 96/64 |
| 4,976,752 | 12/1990 | Torok et al. ................................ 96/97 |
| 5,254,231 | 10/1993 | Heath et al. .............................. 204/164 |

OTHER PUBLICATIONS

Miyaski, Method for Manufacturing of Anion and its Device, May 1992, Translation of Japanese Koki 4–141179.
PTO 96–0438, which is a translation of Japan Koki 5–31198 Feb. 9, 1993.

Primary Examiner—David A. Reifsnyder
Attorney, Agent, or Firm—Kanesaka & Takeuchi

[57] ABSTRACT

The apparatus is formed of a centrifugal force and Coriolis force generating device and a gas and liquid separation device. The centrifugal force and Coriolis force generating device gives high energy to supplied liquid by generating a spirally flowing air stream therein, to thereby ion-dissciate the liquid. Also, it provides energy necessary to micronize and activates the liquid drops with the centrifugal force and Coriolis force acted in the spirally flowing air stream. The activated liquid drops ionize oxygen particles at the gaseous side when electric doublets is oriented on the surface of the liquid drops, thereby causing groups of negative ions to be generated. The gas and liquid separation device separates the gas and liquid sent out from the centrifugal force and Coriolis force generating device and discharges air including negative ions into the atmosphere.

6 Claims, 7 Drawing Sheets

ELECTRIC CHARGE DISTRIBUTION ON THE
GAS AND LIQUID PHASE BOUNDARY

APPARATUS FOR GENERATING NEGATIVE IONS

BACKGROUND OF THE INVENTION

1. Field of the Invention

The present invention relates to an apparatus for generating negative ions with which air can be ionized.

2. Description of the Prior Art

It has been known for a long time that air ions or ions in air greatly influence the health of a human body. Air ions are generated by electrolytic dissociation due to radioactive materials of the earth's crust, cosmic rays in the atmosphere, ultraviolet rays, gaseous oxidization due to heat, and electrolytic dissociation due to lightning discharge. They are also generated by electrification in air accompanied by water drop fission in air. Namely, electrification phenomena during precipitation and in the vicinity of water falls are called the "Lenard Effect" or "Water fall effect", and ions generated in air are negative ions regardless of the electric charge of water drops (Refer to "Atmospheric electrics", page 27, written by Naohisa Hatakeyama and Minoru Kawano and published by Iwanami Publishing Co., Ltd.).

In connection with influences upon human bodies due to positive and negative ions which are generated by electric dissociation of air, it is generally said that positive ions excite the nerves and negative ions tranquilize the nerves. For this reason, it is considered that negative ions generated in air at and around water falls, rivers, and sea shores refresh human bodies and minds.

In recent researches, it has been found that negative ions have a dust eliminating effect, sterilization effect, deordorization and gaseous constituents eliminating effects, and electrification preventing effect, and furthermore have favorable influences on the growth of animals and plants. And attention has been made to negative ions.

Conventionally, a negative ion generating apparatus in which positive and negative ions are generated by utilizing corona discharge and the positive ions are caught while the negative ions are extracted, has been used as a device for artificially generating negative ions. However, it has been found that, when this kind of a device is used, ozone and nitride oxide which are harmful to human bodies are generated as byproducts.

On the other hand, according to the Lenard Effect, it is possible to generate a comparatively large number of negative ions with a small electric power due to only fission of water drops, without generating any harmful materials nor further requiring electric power as necessary when corona discharge is utilized.

Lenard found out through experiments that, in a case where water drops are split when colliding with a metal plate, ions are generated in atmospheric air; the total quantity of electrification of the split water drops becomes larger than the electric quantity of the initial water drops; and the total quantity of electric charge of ions generated in air is equal to the quantity of electricity of the water drops increased through fission. However, thereafter, Simpson repeated Lenard's experiments, carried out measurements by using more accurate devices, and confirmed and reported that only fission of water drops in air brings the results similar to the case of Lenard's ; ions generated in air are negative ions regardless of the electric charge of the water drops; and the water drops have the positive electric charge which is equivalent to number of ions generated in fission ("Atmospheric electrics", pages 26 to 27, written by Hisanao Hatakeyama and Minoru Kawamoto and published by Iwanami Publishing Co., Ltd.).

A method to utilize the Lenard Effect is disclosed in Japanese Laid open Patent Publication No. Hei 4-141179 and No. Hei 5-31198. In the method described in these prior embodiments, in summary, microscopic water drops are formed and mixed with air to take out negative ions by selecting the particle size of the microscopic water drops mixed with air. The method described in the prior embodiments is basically based on the concept that a water jet stream is split or separated by bringing it into collision with a metallic plate. It is deemed that Lenard's experiments are faithfully repeated.

In regard to a mechanism with which ions are generated in air due to fission of water drops, it is explained as follows, in the electrostatic handbook, page 104, ("Electrostatics Academy", Ohm Publishing Co.); namely, in a case where phase $\alpha$ is gas (air) and phase $\beta$ is liquid (water), when high energy (jetting, collision and shedding) is given to water, electric double layers by $H^+$, $OH^-$ due to ion dissociation of water is formed, and at the phase boundary, electric doublets are oriented to form double layers of electric dipole due to the electric dipole moment ($6.17 \times 10^{-3}$ Cm), wherein negative ions are oriented outwards. More negative ions are attracted near the liquid boundary, and positive ions are not pulled so strongly and freely in the liquid. Therefore, positive ions remain in the liquid and are neutralized through grounding. In the case where water drops are ultimately minimized by providing high energy such as jetting, collision, shedding and so on to water, when electric dipole is oriented on the surface of water drops, oxygen ($O_2$) molecules which exist at the phase boundary at the gaseous (air) side are ionized and become groups of negative ions expressed with $O_2^-.(H_2O)n$. These groups of negative ion particles are defined as negative ion added water molecules.

According to the ion generating mechanism described above, it is found that air is ionized by providing high energy to water drops and splitting the water drops. Therefore, in Lenard's case, high energy is given to water drops by bringing water drops into collision with a metallic plate. However, according to Lenard's method employed in the prior embodiments, the energy given to water drops will be determined by the jetting pressure of water and the distance between water jetting nozzles and the metallic plate. So, a pump having a large output must be used to secure high pressure jetting with the distance between the nozzles and the metallic plate adequately maintained.

Japanese Laid Open Patent Publication No. Hei 4-141179 discloses an example of using an ultrasonic humidifier for the purpose of generating minute water drops. However, it is necessary to provide an ultrasonic generator having a high output capacity in order to give high energy to water drops by utilizing ultrasonic waves. Therefore, it can not be said that the ultrasonic humidifier is an effective means from the standpoint of negative ion generation ratio per unit power. As pointed out by Simpson, only fission of water drops in air may produce the same effect as that of Lenard's case.

It is therefore an object of the invention to provide an apparatus for generating negative ions by functionally making clear the mechanism of generating negative ions as much as possible and efficiently utilizing the functions thereof.

It is another object of the invention to provide an apparatus for generating a large amount of negative ions through gas and liquid separation after splitting liquid into minute water drops by utilizing the high energy of a turning air stream.

It is a further object of the invention to provide an apparatus for generating a large amount of negative ions by providing an ion dissociation treatment to the liquid to be split into minute water drops in advance. It is a still further object of the invention to provide an apparatus for splitting the liquid jetted into the turning air stream into micronized water drops by utilizing the centrifugal force generated by the turning air stream and causing a Coriolis force to act on the liquid drops.

It is a further object of the invention to provide an apparatus for jetting liquid into the turning air stream by causing air to flow along a helical portion of a screw guide arranged in a pneumatic feeding conduit and causing spiral movement to the air stream.

It is a further object of the invention to provide an apparatus for jetting liquid drops into the turning air stream by applying to the turning air stream the jetting liquid drops and providing the centrifugal force and Coriolis force to the liquid drops.

DETAILED DESCRIPTION OF THE PREFERRED EMBODIMENTS

A negative ion generation mechanism according to the invention functionally carries out an ion dissociation treatment, liquid drop activation treatment, ionizing treatment of gas particles, and gas and liquid separation treatment in the above order. The respective treatments can not be clearly distinguished from each other. The ion dissociation treatment will be naturally carried out by the activation treatment. However, it is more effective to perform the ion dissociation treatment prior to the activation treatment of liquid drops. The technical meanings of the respective treatments will be described below.

Liquid drops split in air are ion-dissociated and activated to cause gas particles to be ionized, so that liquid or negative ion added water molecules are accordingly generated. The negative ion added water molecules are separated from the water drops by a centrifugal force separation method, and can be extracted and taken out.

In the invention, liquid (water) is jetted into turning stream of gas or spirally flowing gas to thereby be split and receives intensive centrifugal force and Coriolis force which are generated in the turning stream of gas to be thereby ion-dissociated, and the liquid (water) is activated. The Coriolis force is a factor (f) based on the latitude and is one of the assumed forces acting on a moving substance in the rotating coordinate systems. Assuming that the angular speed of rotation is "$\omega$", and the mass of a particle and linear velocity are respectively "m" and "v", Coriolis force is given with an expression of $2\ m \times \omega \times V$. The Coriolis factor (f) which generates Coriolis force is given with the following expression:

$$f = \Omega \sin \Phi$$

Wherein $\Omega$ is the angular speed of the earth's rotation and $\Phi$ is the earth's latitude. The Coriolis force resulting from the earth's rotation reversely acts in the Northern Hemisphere and Southern Hemisphere. As it is to the right side relative to the advancing direction in the Northern Hemisphere, the direction of turning or spiral flowing so that the Coriolis force based on the angular speed vector of the earth's rotation is applied to liquid. By effectively using the Coriolis force, it is possible to obtain energy substantially equal to that given when rain drops fall several hundreds of meters, with a travelling distance of only a few centimeters.

The ion dissociation is an ion dissociation treatment of water. Where liquid (water) is provided with intensive energy, water ($H_2O$) is dissociated as shown below;

$$H_2O \rightarrow H^+ + (OH)^-$$

Figure 1:
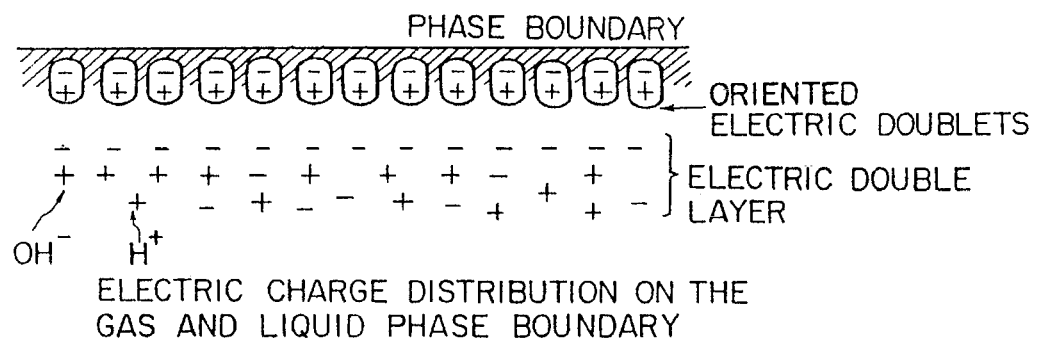
FIG. 1 is a view showing the electrostatic field distribution in the gas and liquid phases.

As shown in FIG. 1, double layers of electric charge are formed in the liquid, and the oriented electric dipole causes negative ions to be oriented outwards on the surface of the liquid adjacent to air, thereby causing negative ions to be more attracted in the vicinity of the liquid surface. Here, if water is mechanically split into small water drops by a certain method, the net electric charge in the water drops is made negative, and the positive ions become large and remain in the water or will be neutralized through grounding (Refer to "Static electricity handbook", page 104 edited by the Static Electricity Academy and published by Ohm Corporation).

As a rule, the ion dissociation has no relation to fission of liquid. Therefore, if liquid is mechanically, electrically, electromagnetically, or optically treated or irradiated with radiant rays prior to fission of liquid drops in air, and the ion-dissociated liquid is split in air, the ionizing thereof is made more effective.

If the ion-dissociated liquid particles are accelerated with high energy given thereto, since the liquid drops are given high energy, ion dissociation and fission of the liquid drops are promoted. Thus, the phase boundary of the liquid drops is activated.

In the activation of the phase boundary of the liquid drops, electric doublets are oriented by the dipole moment of water to thereby form double layers of electric doublets, and negative electric charge is discharged when orienting negative ions outwards.

$H^+:OH^-$ in the liquid drops which are unlimitedly micronized is held together with Van der Waals forces. However, as they are given a strong centrifugal force ($mr\omega^2$) (r is radius) and Coriolis force ($2\ mv\omega$), $H^+$ and $OH^-$ are oriented by the difference of the mass ($H^+=1$, $OH^-=17$), so that $OH^-$ orients outwards. Negative charge are discharged while the electric doublets is being oriented.

Gas particles are necessarily ionized in line with the activation of the liquid drops. The liquid drops are unlimitedly micronized while they are moving with high energy given thereto, and oxygen molecules ($O_2$) which exist at the gas (air) side phase boundary are ionized, thereby generating negative ion added water molecules expressed by $O^-_2 \cdot (H_2O)_n$. It is possible to separate and extract air including negative ion added water molecules from the liquid drops by using a centrifugal force separation method.

In the invention, it is possible to spout liquid at an angle in the direction opposite to the stream of air, in order to split liquid into micro liquid drops in the turning air stream. The velocity of a high speed air stream is faster toward the conduit wall and slower toward the center part as shown in FIG. 5b.

As a result, a great pressure (+P) will be given to the outer circumference in the vicinity of the conduit wall, and the pressure (–P) is smaller at the inner circumference in the vicinity of the center part. When liquid is jetted at a right angle for the air stream direction, the liquid drops are not actively splashed out but may drip at the inner circumferential part. If liquid is jetted in the direction opposite to the stream of air, the splashing degree of the liquid drops will be increased. Furthermore, if the liquid is jetted with revolutions, the liquid drops can reach the outer circumferential part where the air pressure is high while turning in the air stream, and are splashed into the air stream. This is identical to the principle that it is not smooth to remove water from a bottle having a small mouth and filled with water but it is made much easier to remove if water in the bottle is turned. It is preferable to give a spouting energy to the jetting water stream by causing a centrifugal force and Coriolis force to act thereon. Furthermore, in the invention, the centrifugal force and Coriolis force are controlled with the inclination angle and pitch of the screw guide, wherein the pitch of the screw guide is gradually increased from the upstream side, and the start-up angle of the inclination is made small. Therefore, the gas and liquid separation efficiency is increased with less pressure loss of the air stream, and a large amount of negative ion added water molecules are generated.

The gas and liquid separation treatment is for separating air including negative ion added water molecules from liquid drops. It is necessary to carry out the gas and liquid separation quickly before positive and negative ions recombine with each other. Liquid drop particles are substantially separated by a centrifugal force while being turned with intensive centrifugal force action given thereto. Furthermore, the liquid drops are separated with a cyclone separator, and air including negative ion added water molecules is delivered into the atmosphere.

It is possible to optionally take out positive ions left over in the liquid drops as necessary. If not necessary, positive ions are returned into the liquid tank and neutralized by grounding.

Figure 2:
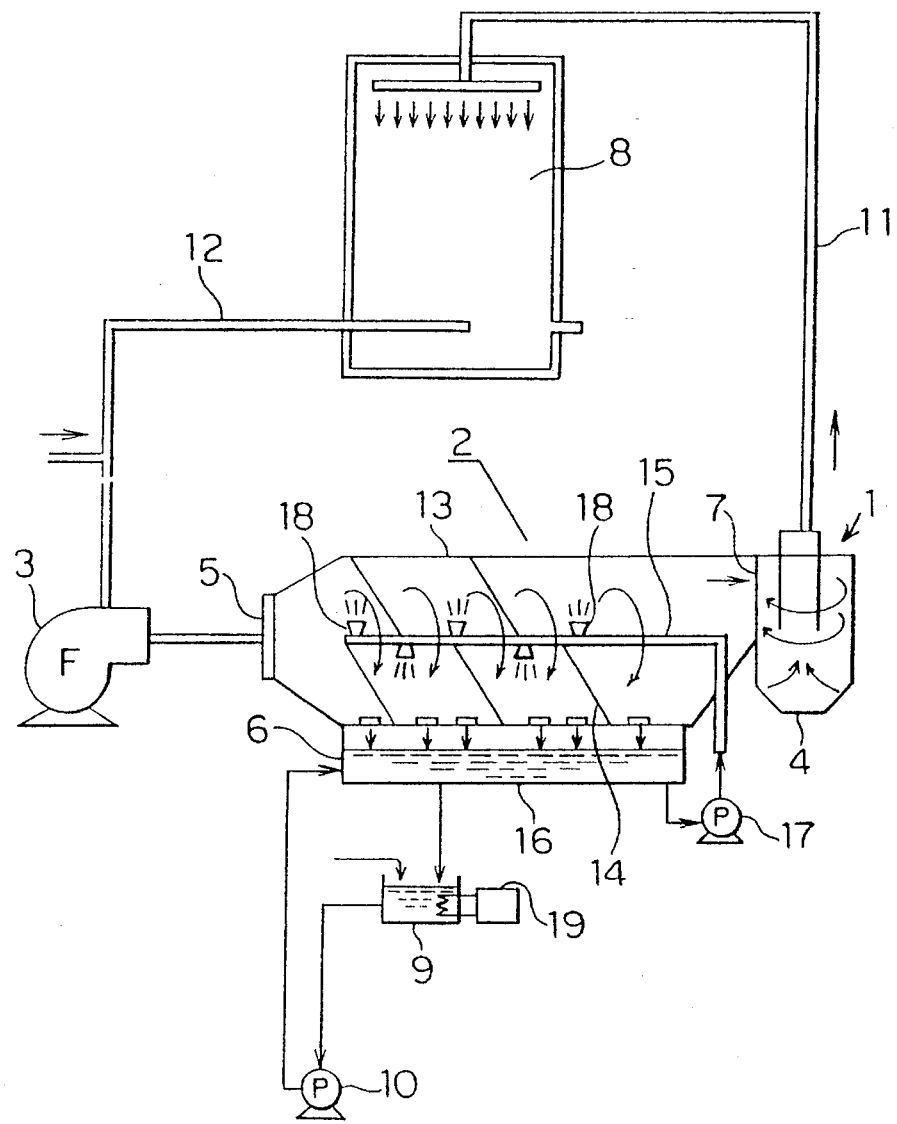
FIG. 2 is a view showing a preferred embodiment of the present invention.

In FIG. 2, the preferred embodiment shows an example where a negative ion generating device 1 is provided outside a chamber 8 where the atmosphere is controlled. The chamber 8 is controlled by an apparatus according to the invention, and it includes houses, offices, refrigerators, foodstuff processing and preserving rooms, clean rooms, growing facilities for animals and plants, etc. The apparatus according to the invention does not aim at controlling the atmosphere of a room, but negative ion added water molecules generated with the apparatus may be utilized for a nebulizer and for washing substances. The negative ion generating apparatus 1 is formed of a combination of a centrifugal force and Coriolis force generating device 2, and a gas and liquid separation device 4.

The centrifugal force and Coriolis force generating device 2 has an air inlet port 5, a liquid inlet port 6, and an air exhaust port 7. A high speed air stream generating device 3 is connected to the air inlet port 5 to supply atmospheric air. The gas and liquid separation device 4 is connected to the air exhaust port 7, and air from which liquid is separated is delivered through the outlet port thereof. A tank 9 is connected to the liquid inlet port 6 via a pump 10 to supply liquid in the tank to the port 6. In the preferred embodiment, an output tubing path 11 of the gas and liquid separation device 4 and input tubing path 12 of the high speed air stream generating device 3 are opened to the controlled chamber 8, thereby forming a circulation system. Furthermore, in the preferred embodiment, the negative ion generating device 1 is provided outside the controlled chamber 8 and is connected to the controlled chamber 8 with tubing paths 11 and 12. However, the negative ion generating device 1 may be installed in the controlled chamber 8, and an air feeding port of the gas and liquid separation device 4 and an air inlet port of the high speed air stream generating device 3 may be opened in the controlled chamber 8, whereby the system may be used as an in-chamber installation type.

The centrifugal force and Coriolis force generating device 2 is a mechanism, wherein ions are dissociated, liquid drops are activated, and air particles are ionized. In the preferred embodiment, the mechanism is such that a screw guide 14 is arranged along the axial center in a horizontal pneumatic feeding conduit 13, a nozzle pipe 15 is provided on the axial center thereof, and a water reservoir 16 is provided on the lower circumferential portion.

Water in the tank 9 is lifted into the water reservoir 16 by the pump 10. The water in the water reservoir 16 is lifted by another pump 17 to be delivered into the nozzle pipe 15. In the preferred embodiment, the tank 9 is provided with a refrigerator device 19, whereby the supplied water is cooled down to a necessary temperature.

Figure 3:
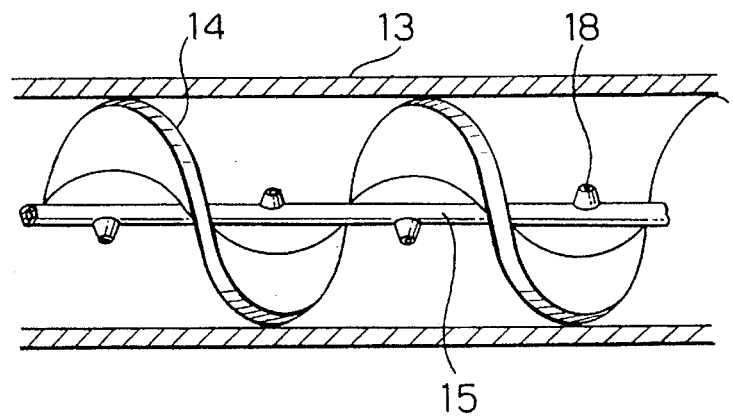
FIG. 3 is a view showing the shape of a screw guide.

The screw guide 14 introduces the air stream into the pneumatic feeding conduit 13 as shown in FIG. 3, and the air stream is spirally turned in the axial direction of the conduit. In the preferred embodiment, the orientation of the air stream turning is regulated by the screw guide 14 so that Coriolis force is oriented in the angular speed vector of the earth's rotation.

On the nozzle pipe 15, nozzles 18 are provided and opened at required portions of the circumferential surface along the axial center thereof, and the nozzles 18 spout liquid supplied from the water reservoir 16 into the turning air stream in the pneumatic feeding conduit 13. In the preferred embodiment, the nozzles 18 form an ion dissociation mechanism. Water is spouted with high pressure from the nozzles 18 and is given energy, thereby causing water to be ionized. As a matter of course, if water which is iondissociated in advance is supplied into the pneumatic feeding conduit 13, the ions will be more dissociated.

The high speed air stream generating device 3 is a fan for an air blower. In the preferred embodiment, it absorbs air in the controlled chamber 8 and delivers air into the pneumatic feeding conduit 13 via the air inlet port 5.

In the preferred embodiment, a cyclone separator is used as the gas and liquid separation device 4. The cyclone separator is effective as far as a predetermined wind velocity and/or pressure is obtained for the air stream including minute water drops and is discharged from the air exhaust port 7 of the pneumatic feeding conduit 13. Air separated from the liquid is introduced into the controlled chamber 8 via the tubing path 11.

Figure 4A:
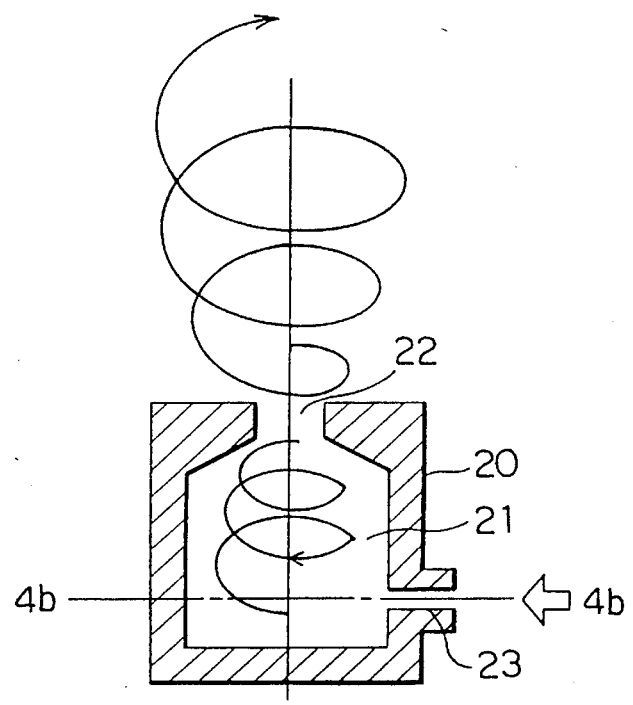
FIG. 4a is a sectional front elevation view of a nozzle.
Figure 4B:
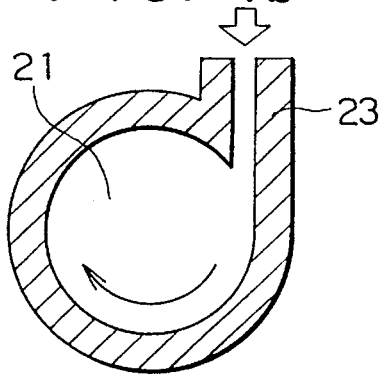
FIG. 4b is a cross-sectional view taken along the line 4b—4b of FIG. 4a, FIG. 5a is a view showing a jetting angle of a liquid to a turning stream of gas.

As shown in FIGS. 4a and 4b, the nozzle 18 includes a nozzle casing 20 having a cylindrical nozzle chamber 21, the upper part of which is conical. The casing 20 has a nozzle port 22 at the top central portion of the nozzle chamber 21, and a liquid supply port 23 opened in the tangential direction of the bottom thereof. Therefore, the compressed water supplied with pressure from the nozzle pipe is turned in the nozzle chamber 21, and the motion energy ($\frac{1}{2}$ mv$^2$) thereof is added with a centrifugal force (mr$\omega^2$) and Coriolis force (2 mv$\omega$). Then, the compressed water is energetically ejected from the nozzle port 22 while turning and extending radially outwardly.

Figure 5A:
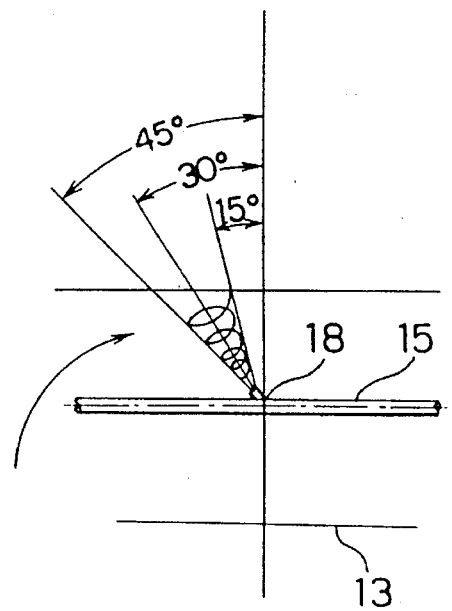
FIG. 5b is a view showing an expansion of split water drops.
Figure 5B:
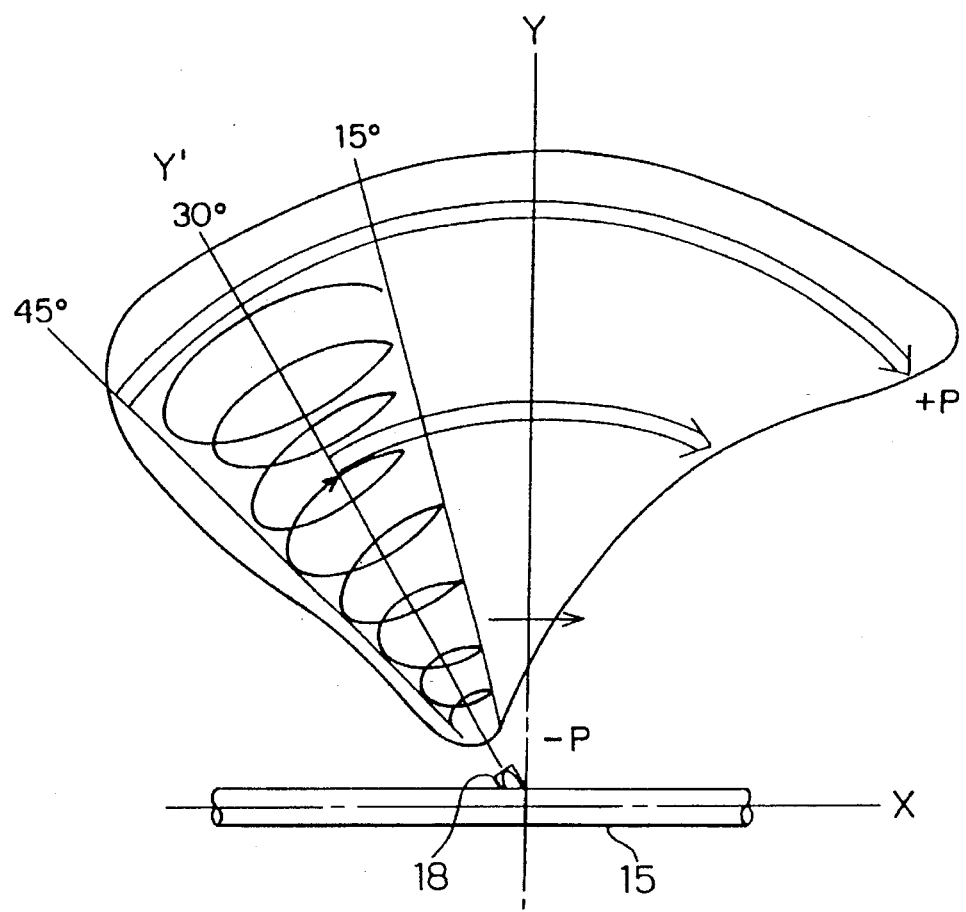

As shown in FIG. 5a, the nozzles are oriented with some degrees in the direction opposite to the stream of air flow turning in the pneumatic feeding conduit 13. As shown in FIG. 5b, the jetting water is spouted or ejected into the turning air stream against the air stream direction, thereby causing water drops to be effectively split. A preferable spouting angle of the jetting water stream is 15 to 45 degrees relative to the vertical direction of the conduit axis, where it is possible to obtain the greatest effect. In this connection, in a case where water drops are ejected in the vertical direction for the conduit axis, the number of generated negative ions was one tenth or less.

Figure 6:
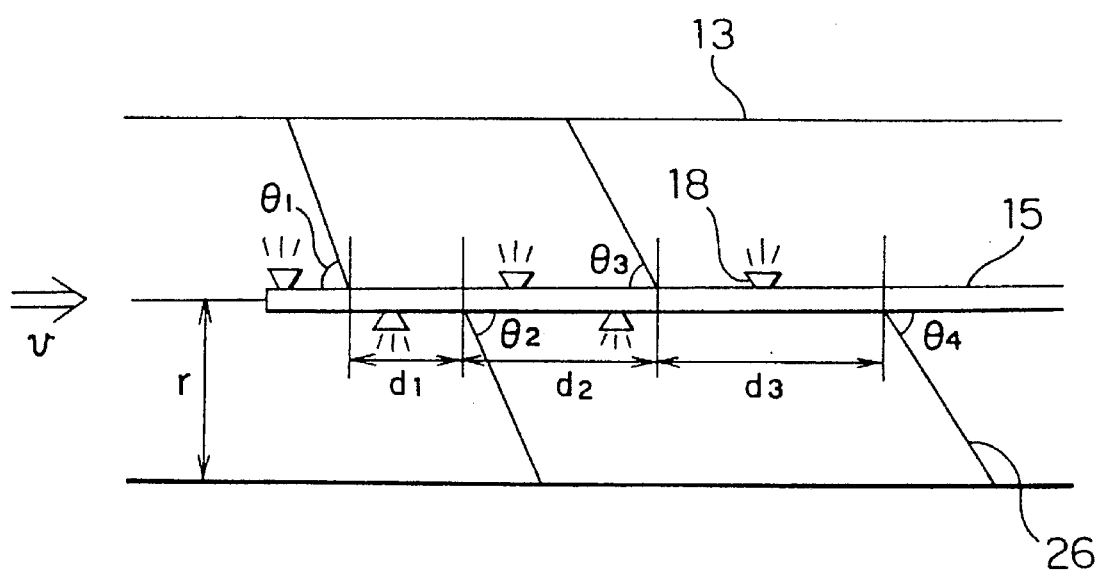
FIG. 6 is a view showing the pitch and inclination angle of the screw guide.

It is necessary to install the screw guide 14 so as to cover at least some distance in the air inlet side of the pneumatic feeding conduit in order to form a Coriolis force. In FIG. 6, in a case where the screw guide 14 is provided to extend two or more turns, the spiral pitch of the screw guide 14 is gradually increased from a side of the air inlet port 5 toward the air exhaust port 7, and the pitch is changed in the order of $d_1 \ll d_2 \ll d_3$, thereby gradually decreasing the angular speed vector ($\omega$) of the turning air stream, and the centrifugal force (mr$\omega^2$) and Coriolis force (2 mv$\omega$) are accordingly weakened to decrease the pressure loss.

The inclination angle of the screw guide 14 is decreased from the side of the air inlet port 5 toward the air exhaust port 7 in the order of $\theta_1 \gg \theta_2 \gg \theta_3 \gg \theta_4$. As a result, the inclination angle will be decreased in line with the increase of the spiral pitch of the screw guide 14. The resistance due to the centrifugal force and Coriolis force can be lessened to decrease the pressure loss by setting the inclination angle at the utmost leading tip of the screw guide 14 to a smaller value than the earth's latitude ($\Phi$) at the installation place of the negative ion generating device.

Figure 7A:
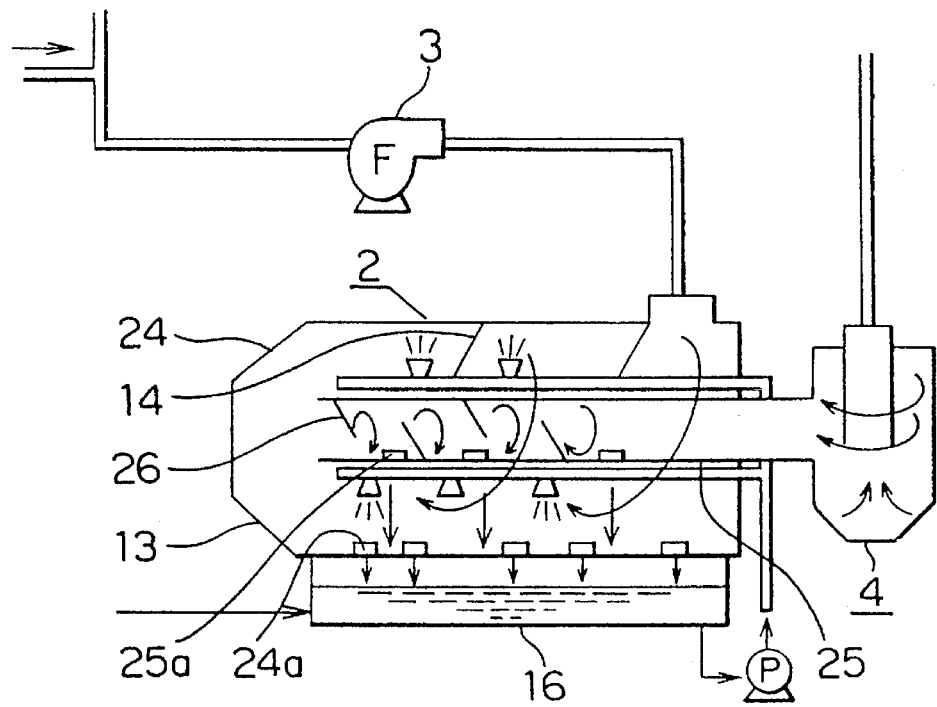
FIG. 7a is a view showing another preferred embodiment of the invention.
Figure 7B:
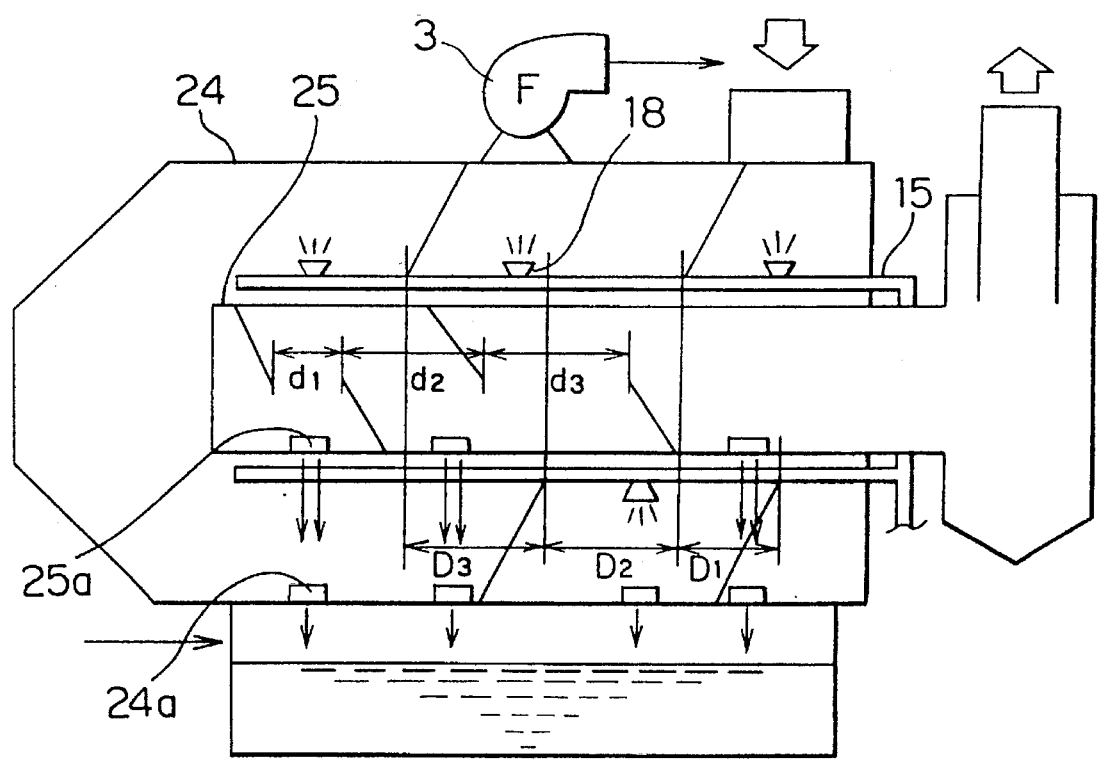
FIG. 7b is a view showing the pitch and inclination angle of the screw guide.

FIGS. 7a and 7b show another preferred embodiment of the invention. In the preferred embodiment, the pneumatic feeding device of the centrifugal force and Coriolis force generating device has inner and outer double structures, and this is an example of the preferred embodiment wherein the feeding distance is increased with the same length of the device. An inner cylinder 25 is provided coaxially with the outer cylinder 24 of the pneumatic feeding conduit, and one end of the inner cylinder 25 is opened to the outer cylinder 24, and the end thereof is connected to the gas and liquid separation device 4.

In the preferred embodiment, the air stream spouted from the high speed air stream generating device 3 is turned on the outer circumference of the inner cylinder 25, reversed at the end of the pneumatic feeding conduit 13 and introduced into the inner cylinder 25. And while the air stream is turning, it is sent to the gas and liquid separation device 4. Furthermore, in the preferred embodiment, the nozzles 18 are provided on the outer circumference of the inner cylinder 25.

Furthermore, a screw guide 14 is provided between the inner cylinder 25 and outer cylinder 24 so that a high speed air stream flows into the angular speed vector direction due to the earth's rotation, and a screw guide 26 is also provided in the angular speed vector direction due to the earth's rotation inside of the inner cylinder 25. Since the inner cylinder is provided with many pore 25a, water drops splashed with a centrifugal force and Coriolis force outside the inner cylinder 25 are further splashed with a centrifugal force and Coriolis force when passing through the inner cylinder 25, thereby providing high energy to the water drops.

Furthermore, the screw guide 14 may not be necessarily provided in the outer cylinder. However, it is necessary to spirally provide a screw guide in the inner cylinder so as to extend for a fixed range from the inlet side, preferably at least one turn. The nozzle structure and spouting angle of liquid are identical to those in the first preferred embodiment.

The pitch of the screw guide 14 in the outer cylinder is gradually increased in the order of:

$$D_1 \ll D_2 \ll D_3$$

The pitch of the screw guide 26 in the inner cylinder is gradually increased in the order of:

$$d_1 \ll d_2 \ll d_3$$

All the other conditions are identical to those in the first preferred embodiment. Water passing holes 24a, 25a are provided at the inner cylinder 25 and outer cylinder 24.

In the preferred embodiment, it is possible to more effectively dissociate ions, activate liquid drops and ionize air particles than with the first preferred embodiment and possible to generate a large amount of negative ions while decreasing the number of positive ions in the supplied air. The preferred actual embodiments of the invention are described hereinafter:

(Embodiment 1) Number of ions in the supplied air was measured by using a negative ion generating device shown in FIG. 2. The specification thereof and measurement conditions are as follows:

| 1. Centrifugal force and Coriolis force generating device | | | |
|---|---|---|---|
| (1) | Pneumatic feeding conduit | | |
| | Conduit diameter (2r) = (2 × 600) | 1200 mm dia. | |
| | Conduit length (1) | 3080 mm | |
| | Inlet diameter | 436 mm dia. | |
| | Outlet diameter | 510 mm dia. | |
| (2) | Nozzle pipe | 50 mm dia. | |
| | Nozzle outlet diameter | 3 mm dia. | |
| | Number of nozzles | 30 | |
| | Nozzle installation angle | 30 deg. | |
| (3) | Guide plate | | |
| | Scerw guide | One turn | |
| | Guide angle ($\theta_1$) | 53 deg. | |
| | Pitch (distance) ($d_1$) | 220 mm | |
| 2. Running condition | | Inlet | Outlet |
| Air volume (m$^3$/min.) | | 120 | 120 |
| Line velocity (m/sec.) | | 12 | 8 |
| Temperature (°C.) | | 19 | 18.5 |
| Humidity (%) | | 46 | 88 |
| Water temperature (°C.) | | 18 | — |
| Water pressure (Kgf/cm$^2$) | | 0.8 | — |

According to the results of the measurement, the number of negative and positive ions in the supplied air is as follows:

| Negative ions (ions per cc) | 90 | 550,000 |
|---|---|---|
| Positive ions (ions per cc) | 60 | 1,600 |

Figure 8:
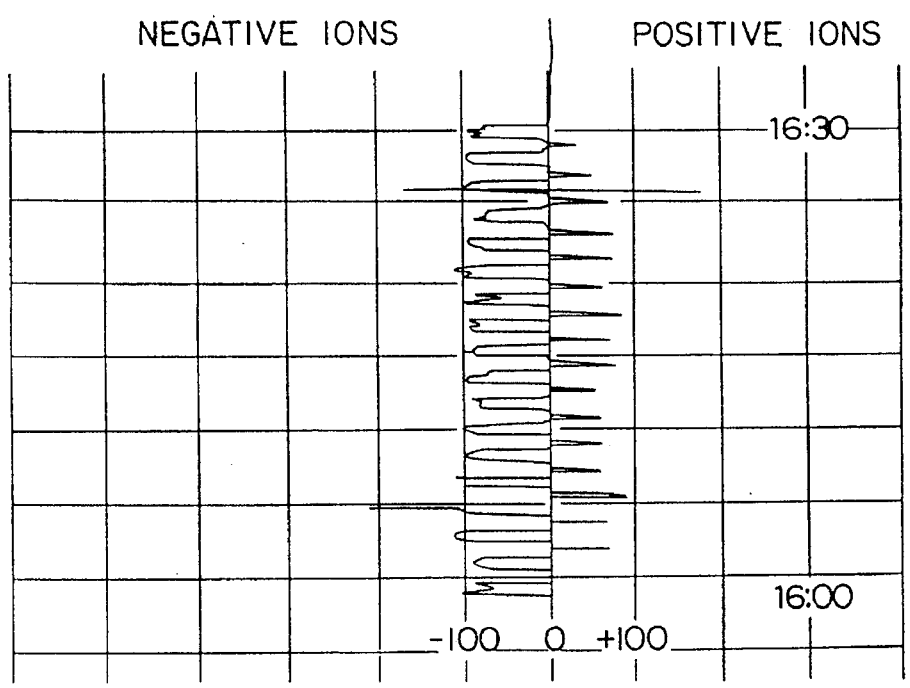
FIG. 8 is a view showing the measurement data of the air ion quantity in the atmosphere.
Figure 9:
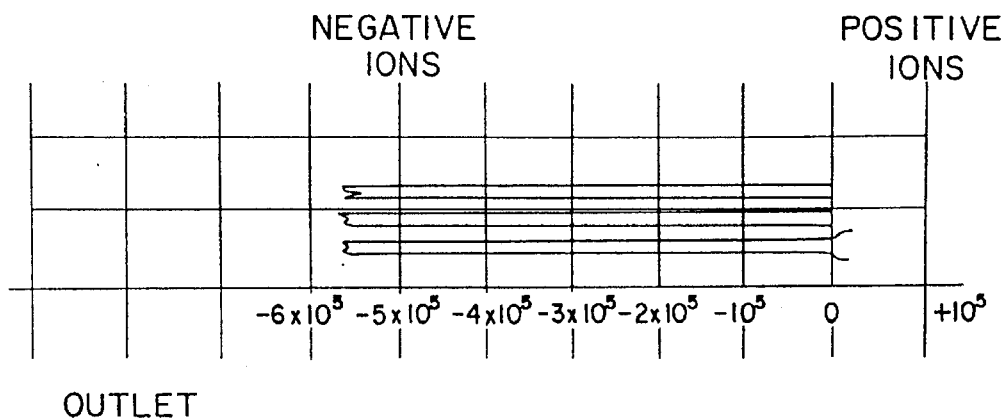
FIG. 9 is a view showing the measurement data of the air ion quantity.

FIG. 8 shows the number of negative ions and positive ions in the atmosphere at the place where a negative ion generating apparatus is installed. As made clear in FIG. 9, the average number of negative ions is 550,000 ions per cubic centimeter at the outlet of the apparatus and the average number of positive ions is 1,600 ions per cubic centimeter at the same place. According to FIG. 8, the average number of negative ions in the atmosphere is 90 ions per cubic centimeter and the average number of positive ions is 60 ions per cubic centimeter.

(Embodiment 2) The number of ions in the supplied air was measured by using a negative ion generating apparatus shown in FIG. 7. The specifications thereof and running conditions are as follows:

1. Pneumatic feeding conduit

| | | |
|---|---|---|
| (1) | Outer cylinder | |
| | Conduit diameter (2R) | = 1200 mm dia. |
| | Conduit length (L) | = 3080 mm |
| | Inlet dimensions | = 500 × 300 mm |
| (2) | Outer cylinder nozzle | |
| | Nozzle pipe | 50 mm dia. |
| | Nozzle outlet diameter | 3 mm dia. |
| | Number of nozzles | 30 |
| | Nozzle installation angle | 30 deg. |
| (3) | Outer cylinder angle | |
| | Screw guide | One turn |
| | Guide plate angle | 53 deg. |
| | Pitch (Distance) ($D_1$) | 280 mm |
| (4) | Inner cylinder | |
| | Conduit diameter (2r) | = 510 mm dia. |
| | Conduit length (L) | = 2050 mm |
| | Outlet dimensions | = 510 mm dia. |
| (5) | Inner cylinder guide | |
| | Screw guide | One turn |
| | Pitch (Distance) ($d_1$) | 255 mm |

| 2. Running condition | Inlet | Outlet |
|---|---|---|
| Air volume (m³/min.) | 120 | 120 |
| Line velocity (m/sec.) | 12 | 8 |
| Temperature (°C.) | 19 | 18.5 |
| Humidity (%) | 45 | 89 |
| Water temperature (°C.) | 18 | — |
| Water pressure (Kgf/cm²) | 1 | — |

According to the results of the measurement, the number of negative ions in the supplied air is 610,000 ions per cubic centimeter, and the number of positive ions is 1,800 ions per cubic centimeter.

The following respective embodiments are examples in which liquid ion-dissociated in advance is split or ejected in air. Ultraviolet ray application, magnetic field application and mechanical water agitation are respectively carried out for ion dissociation.

Figure 10:
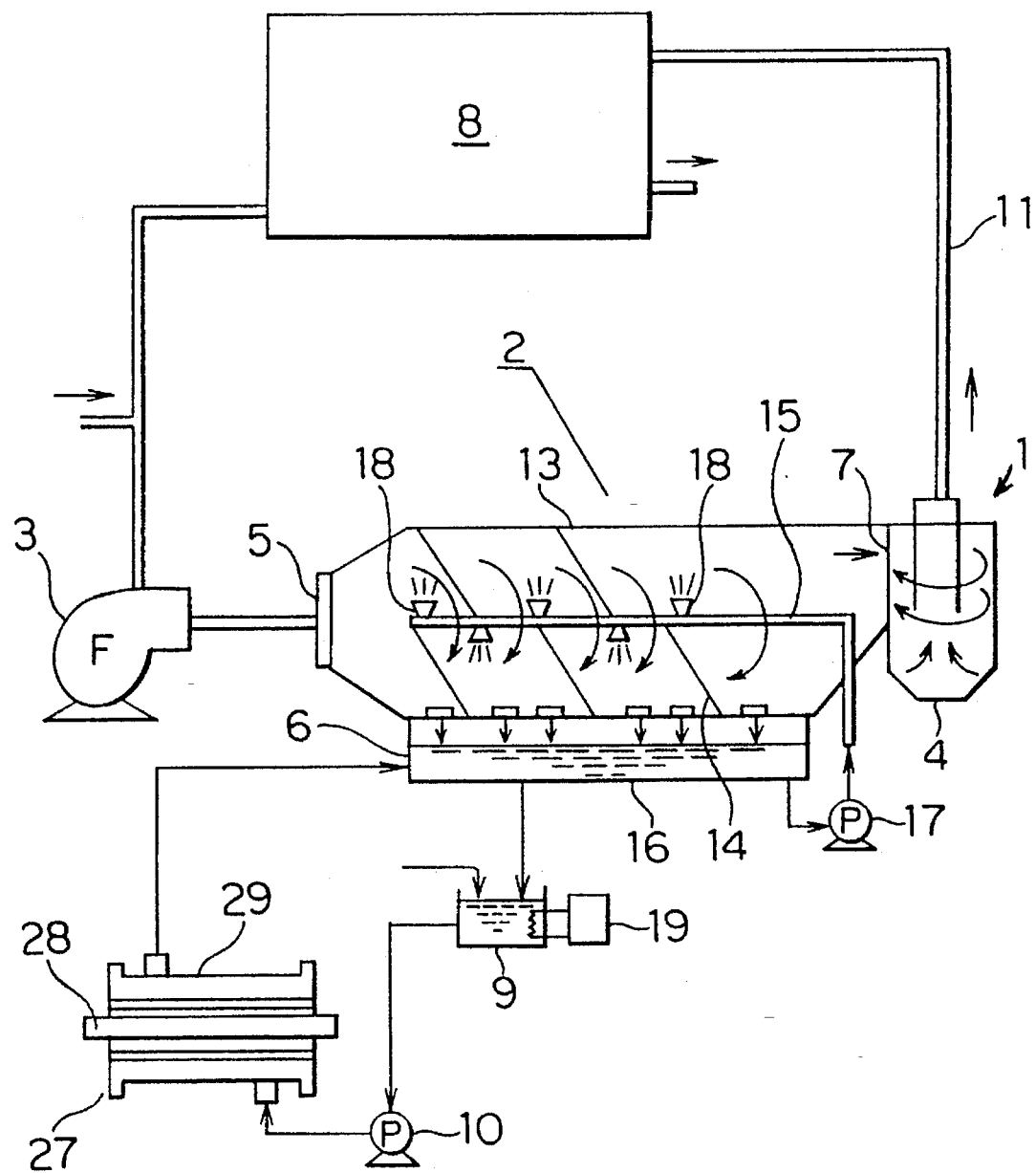
FIG. 10 is a view showing a preferred embodiment separately provided with an ion dissociation device.

(Embodiment 3) In FIG. 10, a low voltage mercury lamp (2 kW) device wherein the peak of ultraviolet ray wavelength is 253.7 nm is used in an ion dissociation device 1, and the tank 9 is filled with city water (A) or distilled water (B). Ultraviolet rays generated by the low voltage mercury lamp 28 of an ion dissociation device 27 are applied to the liquid in a casing 29 supplied by a pump 10 from the tank 9, thereby ion-dissociating the liquid. The ion-dissociated liquid is supplied to a horizontal centrifugal force and Coriolis force generating device 2 at a supplying volume of 66 liters per minute and at a supplying pressure of 0.5 Kgf/cm². Thereafter, the liquid is spouted through the nozzles by a pump 17 at a supplying volume of 66 liters per minute and at a supplying pressure of 1.5 Kgf/cm². On the other hand, the atmospheric air is taken in by a high speed air stream generating device 3 at a volume of 20 cubic meters per minute and is supplied at a line velocity of 11 meters per second, into the centrifugal force and Coriolis force generating device 2 having a guide 14 attached thereto at an inclination angle of 53 degrees at a fixed pitch. After the laminar flow treatment, air is discharged into the atmosphere as supplying air at a line velocity of 8.5 meters per second, and ions in this supplying air were measured. The characteristics of the atmospheric air and supplying air are shown in Table 1.

TABLE 1

| | City water | | Distilled water | |
|---|---|---|---|---|
| Items | Atmospheric air | Supplying air | Atmospheric air | Supplying air |
| Temperature (°C.) | 17.5 | 17.1 | 17.5 | 17.4 |
| Relative humidity (%) | 43.6 | 86.2 | 43.6 | 86.0 |
| Positive ions (Ions per cubic centimeter) | $0.6 \times 10^2$ | $2 \times 10^3$ | $0.6 \times 10^2$ | $5 \times 10^3$ |
| Negative ions (Ions per cubic centimeter) | $0.8 \times 10^2$ | $4 \times 10^4$ | $0.8 \times 10^2$ | $5.5 \times 10^4$ |

(Embodiment 4) In an ion dissociation device 1, water was treated. Namely a clearance of 15 mm wide is formed between barium ferrite ($BaO \cdot 6Fe_2O_3$) sintered substances (20×300×200 mm), which generate a space magnetic field of 3,000 gauss and thin wires having a diameter of 1 mm are packed therebetween. Water is supplied in the same conditions as those in the embodiment 1 and is further sent into the water reservoir 16, wherein the water is treated in the same conditions as those in the above. Then, ions in air were measured. The characteristics of the atmospheric air and supplying air are shown in Table 2.

TABLE 2

| | City water (A) | |
|---|---|---|
| Item | Atmospheric air | Supplying air |
| Temperature (°C.) | 28 | 29 |
| Relative humidity (%) | 77 | 98 |
| Positive ions (Ions per cubic centimeter) | $0.5 \times 10^2$ | $2 \times 10^3$ |
| Negative ions (Ions per cubic centimeter) | $0.5 \times 10^2$ | $3.2 \times 10^4$ |

As made clear from Tables 1 and 2, the number of positive ions in the supplying air after treatment is slightly increased in either embodiments. However, the number of negative ions is indeed increased 100 to 1000 times.

Table 3 shows the characteristics of air and water in the embodiment 1 shown in Table 1. As a result, it is clear that the supplying air which is extracted as negative ions does not contain any impurities.

TABLE 3

Results of the experimental analysis with city water used

| | Atmospheric air (μg/m³) | Supplying air (μg/m³) | Circulating water (mg/l) | Condensed water (mg/l) |
|---|---|---|---|---|
| Na | <0.5 | <0.5 | 17 | 0.02 |
| K | — | — | 5.5 | <0.005 |
| Ca | — | —/ 12 | 0.43 | |
| Si | <0.05 | <0.05 | — | — |
| Mg | — | — | 7.3 | 0.029 |
| $NO_x$ (as $NO_3$) | 2 | <2 | — | — |
| $SO_x$ (as $SO_4$) | 4 | <3 | — | — |
| $Cl^-$ | <1 | <1 | 11 | 0.01 |
| $NO_3^-$ | — | — | 0.36 | <0.03 |
| $SO_4^{2-}$ | — | — | 1.2 | 0.07 |

(Note)
1. The circulating water means water in the water resercoir 16.
2. The condensed water means water condensed and obtained by cooling the supplying air by a cooling device.

In Table 4, (A) is an example in which diesel engine exhaust gas and HCI gas are forcibly blown into as the atmospheric air, and (B) is an example wherein an agricultural drug containing captan having a formula 1 is forcibly sprayed as the atmospheric air.

TABLE 4

| | Atmospheric air (μg/m³) | Supplying air (μg/m³) | Circulating water (mg/l) | Condensed water (mg/l) |
|---|---|---|---|---|
| (A) Results of the experimental analysis when being treated with diesel engine exhaust gas and HCL gas, and results of the experimental analysis with city water used | | | | |
| $NO_x$ (as $NO_3$) | 56 | 3 | — | — |
| $SO_x$ (as $SO_4$) | 170 | 35 | — | — |
| $NO_3^-$ | — | — | 0.80 | 0.14 |
| $SO_4^{2-}$ | — | — | 4.8 | 0.21 |
| $Cl^-$ | 2600 | 60 | 120 | 8 |
| (B) Results of the experimental analysis when being treated with an argicultural drug (orthosite wettable agent), and results of the experimental analysis with city water used | | | | |
| Captan (80%) | 1700 | <3 | 3.1 | 0.004 |

Captan

Formula 1

[Structural formula of captan showing cyclohexene ring fused to N-S-C(Cl)₃ group with two carbonyl oxygens]

As seen in the example, it is made clear that the supplying air extracted as negative ions does not have any impurities.

As described above, in the invention, the functions such as ion dissociation, liquid drop activation and ionization of gas particles and gas and liquid separation are carried out. Especially, the water drops are pneumatically fed while applying a centrifugal force and Coriolis force. Then, the Simpson Effect is generated in the pipe to ionize air while the gas and liquid separation is being carrying out. Thus, the chances of recombination of positive and negative ions are reduced, and it is possible to generate a large amount of negative ions by using an apparatus having a small capacity.

In the invention, it is possible to establish the environmental conditions including a large amount of negative ions which exert favorable influences on animals and plants without any harmful constituents, and furthermore, it is possible to obtain various excellent effects which are preferably exerted on the growth of animals and plants, such as dust eliminating effect, sterilization effect, deodorization effect, gaseous constituent eliminating effect, humidity controlling effect, electrification preventing effect, etc.

What is claimed is:

1. A negative ion generating apparatus, comprising, an air stream generating device, a centrifugal force and Coriolis force generating device including a cylindrical air feeding conduit connected to the air stream generating device and being formed of concentric inner and outer cylinders, a spiral guide situated in the feeding conduit for providing a spirally flowing air stream in the feeding conduit along the spiral guide when air is supplied to the air feeding conduit from the air stream generating device, and liquid jetting nozzles situated in a space between the inner and outer cylinders of the feeding conduit to provide air inhaled into the outer cylinder with liquid from the jetting nozzles while air is spirally flowing in said space so that when the liquid is jetted into the spirally flowing air stream in the feeding conduit through the jetting nozzles, liquid drops ejected from the nozzles receive centrifugal force and Coriolis force by the spirally flowing air stream to form liquid particles with negative ions in air, and an air and liquid separation device attached to the cylindrical air feeding conduit for separating the liquid particles from air, said air passing through said space and entering into the inner cylinder to exit to the air and liquid separation device.

2. A negative ion generating apparatus according to claim 1, wherein said jetting nozzle includes means to provide to the liquid a spirally rotating force so that the liquid is jetted with centrifugal force and Coriolis force.

3. A negative ion generating apparatus according to claim 2, wherein said jetting nozzles are oriented to obliquely face an air flowing direction of the spirally flowing air stream in the feeding conduit.

4. A negative ion generating apparatus according to claim 1, further comprising a nozzle pipe situated outside and along the inner cylinder, said liquid jetting nozzles being attached to the nozzle pipe to receive the liquid through the nozzle pipe.

5. A negative ion generating apparatus, comprising, a centrifugal force and Coriolis force generating device including an air feeding conduit formed of concentric inner and outer cylinders, a spiral guide situated in the feeding conduit for providing a spirally flowing air stream in the feeding conduit, and liquid jetting nozzles situated between the inner and outer cylinders so that when liquid is jetted into the spirally flowing air stream in the outer cylinder through the jetting nozzles while air is supplied into the feeding conduit, liquid drops ejected from the nozzles receive centrifugal force and Coriolis force to form liquid particles with negative ions in air, said air passing through the outer cylinder and entering into the inner cylinder, and an air and liquid separation device attached to the inner cylinder of the generating device, said air in the inner cylinder exiting to the air and liquid separation device separating the liquid particles from air.

6. A negative ion generating apparatus, comprising, an air stream generating device, a centrifugal force and Coriolis force generating device including a cylindrical air feeding conduit connected to the air stream generating device, a spiral guide situated in the feeding conduit for providing a spirally flowing air stream in the feeding conduit along the spiral guide when air is supplied to the air feeding conduit from the air stream generating device, a nozzle pipe situated in a center of the air feeding conduit, and liquid jetting nozzles attached to the nozzle pipe and situated in the feeding conduit so that when liquid is jetted into the spirally flowing air stream in the feeding conduit through the jetting nozzles, liquid drops ejected from the nozzles receive centrifugal force and Coriolis force by the spirally flowing air stream to form liquid particles with negative ions in air, and an air and liquid separation device attached to the cylindrical air feeding conduit for separating the liquid particles from air.

* * * * *